(12) United States Patent
Chen et al.

(10) Patent No.: US 11,786,608 B2
(45) Date of Patent: Oct. 17, 2023

(54) ISOQUINOLINYL TRIAZOLONE COMPLEXES

(71) Applicants: Takeda Pharmaceutical Company Limited, Osaka (JP); Rongliang Chen, San Diego, CA (US); Padma Manam, San Diego, CA (US); Lu Zeng, San Diego, CA (US)

(72) Inventors: Rongliang Chen, San Diego, CA (US); Padma Manam, San Diego, CA (US); Lu Zeng, San Diego, CA (US)

(73) Assignee: Takeda Pharmaceutical Company Limited, Osaka (JP)

( * ) Notice: Subject to any disclaimer, the term of this patent is extended or adjusted under 35 U.S.C. 154(b) by 113 days.

(21) Appl. No.: 17/145,006

(22) Filed: Jan. 8, 2021

(65) Prior Publication Data
US 2021/0138086 A1 May 13, 2021

Related U.S. Application Data

(63) Continuation of application No. 16/089,881, filed as application No. PCT/US2017/025076 on Mar. 30, 2017, now abandoned.

(60) Provisional application No. 62/316,520, filed on Mar. 31, 2016.

(51) Int. Cl.
| | |
|---|---|
| *A61K 47/69* | (2017.01) |
| *C07D 401/14* | (2006.01) |
| *A61K 31/4725* | (2006.01) |
| *A61K 31/519* | (2006.01) |
| *C08B 37/16* | (2006.01) |

(52) U.S. Cl.
CPC ...... *A61K 47/6951* (2017.08); *A61K 31/4725* (2013.01); *A61K 31/519* (2013.01); *C07D 401/14* (2013.01); *C08B 37/0015* (2013.01)

(58) Field of Classification Search
CPC .......... C07D 401/14; C08B 37/0015; A61K 31/519; A61K 31/4725; A61K 47/6951
See application file for complete search history.

(56) References Cited

PUBLICATIONS

Cao, X. et al., Journal of Medicinal Chemistry, "Design, Synthesis, and Structure-Activity Relationship Studies of Novel Fused Heterocycles-Linked Triazoles with Good Activity and Water Solubility", 2014, vol. 57, pp. 3687-3706 (Year: 2014).*

Dziedzic, p et al., Journal of the American Chemical Society, "Design, Synthesis, and Protein Crystallography of Biaryltriazoles as Potent Tautomerase Inhibitors of Macrophage Migration Inhibitory Factor", 2015, vol. 137, pp. 2996-3003 (Year: 2015).*

* cited by examiner

*Primary Examiner* — Bahar Craigo
(74) *Attorney, Agent, or Firm* — Matthew J. Russo

(57) ABSTRACT

Disclosed is a complex of a compound of Formula 1,

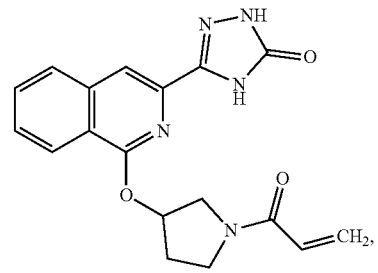

a stereoisomer thereof, or a tautomer of the compound of Formula 1 or stereoisomer thereof, and a cyclodextrin, in which the complex is an amorphous solid. This disclosure also relates to materials and methods for preparing the complex, to pharmaceutical compositions which contain the complex, and to the use of the complex to treat Type I hypersensitivity reactions, autoimmune diseases, inflammatory disorders, cancer, non-malignant proliferative disorders, and other conditions associated with BTK.

11 Claims, 2 Drawing Sheets

ISOQUINOLINYL TRIAZOLONE COMPLEXES

FIELD OF THE INVENTION

This invention relates to isoquinolinyl triazolone complexes which are inhibitors of Bruton's tyrosine kinase (BTK) and to materials and methods used to prepare the complexes. This invention also relates to pharmaceutical compositions which contain the isoquinolinyl triazolone complexes, and to the use of the complexes to treat diseases, disorders, and conditions associated with BTK.

BACKGROUND OF THE INVENTION

BTK is a member of the TEC family of non-receptor protein tyrosine kinases, and it is involved in the regulation of B-cell development, activation, and survival through B-cell antigen receptor (BCR) signaling. See W. N. Khan et al., *Immunity* 3:283-299 (1995); and A. B. Satterthwaite and O. N. Witte, *Immunol. Rev.* 175:120-127 (2000). Mutation of the gene encoding BTK in humans leads to a condition known as X-linked agammaglobulinemia (XLA), which is characterized by reduced immune function, including impaired maturation of B cells, decreased levels of immunoglobulin and peripheral B cells, diminished T-cell independent immune response, and attenuated calcium mobilization following BCR stimulation. See F. S. Rosen et al., *N. Engl. J. Med* 333(7):431-440 (1995); and J. M. Lindvall et al., *Immunol. Rev.* 203:200-215 (2005).

BTK's key role in B-cell development and the BCR signaling pathway suggests that inhibition of BTK may provide therapeutic benefit for the treatment of lymphoma, inflammatory disorders, and autoimmune diseases, among others. Clinical studies involving the depletion of mature B cells via treatment with rituximab indicate that rheumatoid arthritis, systemic lupus erythematosus (SLE), and multiple sclerosis may result from the over expression of B cells. See J. C. Edwards et al., *N. Engl. J. Med.* 350:2572-81 (2004); C. Favas and D. A. Isenberg *Nat. Rev. Rheumatol.* 5:711-16 (2009); and S. L. Hauser et al. *N. Engl. J. Med.* 358:676-88 (2008). Other studies suggest that the BCR pathway may be involved in the survival of tumor cells in non-Hodgkin lymphoma and diffuse large B-cell lymphoma. See R. Küppers, *Nat. Rev. Cancer* 5:251-62 (2005); and R. E. Davis et al., *Nature* 463:88-92 (2010). In preclinical studies, BTK-deficient mice have demonstrated decreased disease progression in murine models of SLE and resistance to collagen-induced arthritis. See M. J. Shlomchik et al., *J. Exp. Med.* 180:1295-1306 (1994); and L. Jansson and R. Holmdahl, *Clin. Exp. Immunol.* 94(3):459-65 (1993). Furthermore, a selective irreversible BTK inhibitor has been shown to completely suppress collagen-induced arthritis in mice, to inhibit autoantibody production and the development of kidney disease in a mouse model for SLE, and to induce objective clinical responses in dogs with spontaneous B-cell non-Hodgkin lymphoma. See L. A. Honigberg et al., *Proc. Natl. Acad. Sci. USA* 107(29):13075-80 (2010).

Certain inhibitors of Bruton's tyrosine kinase are described in WO 99/54286 A2, WO 2002/50071 A1, WO 2007/087068 A2, WO 2008/039218 A2, WO 2008/121742 A2, WO 2007/147771 A2, WO 2009/077334 A1, WO 2009/098144 A1, WO 2009/156284 A1, WO 2010/000633 A1, WO 2010/006947 A1, WO 2008/033834 A1, WO 2010/056875 A1, WO 2010/068788 A1, and WO 2010/068810 A2.

Published international application WO 2014/164558 A1 (the '558 application) describes the preparation, characterization, and use of various pyridinyl and fused pyridinyl triazolones which are inhibitors of BTK. Included among the compounds in the '558 application is the isoquinolinyl triazolone, (S)-3-(1-((1-acryloylpyrrolidin-3-yl)oxy)isoquinolin-3-yl)-1H-1,2,4-triazol-5(4H)-one. See Example 5 of the '558 application. Though a potent inhibitor of BTK, the crystalline compound prepared in Example 5 in the '558 application has low aqueous solubility, which may limit its adsorption and bioavailability following oral dosing.

SUMMARY OF THE INVENTION

This invention provides solid complexes of isoquinolinyl triazolones and cyclodextrin. The complexes are amorphous solids which exhibit improved aqueous solubility and bioavailability over the corresponding crystalline forms of the compounds. This invention also provides materials and methods for preparing the complexes, pharmaceutical compositions which contain the complexes, and the use of the complexes to treat diseases, disorders, and conditions associated with BTK.

One aspect of the invention provides a complex comprising a compound of Formula 1,

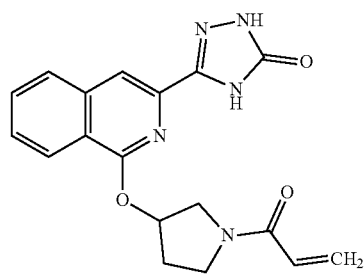

a stereoisomer thereof or a tautomer of the compound of Formula 1 or stereoisomer thereof,
and a cyclodextrin, wherein the complex is an amorphous solid.

Another aspect of the invention provides a pharmaceutical composition which includes a complex as defined above; and a pharmaceutically acceptable excipient.

A further aspect of the invention provides a method of making a complex as defined above, the method comprising atomizing a liquid solution into droplets, the liquid solution comprising a compound, stereoisomer or tautomer as defined above, a cyclodextrin derivative, and water, and removing at least a portion of the water from the droplets to form the complex.

An additional aspect of the invention provides a complex as defined above for use as a medicament.

Another aspect of the invention provides a complex as defined above, for the manufacture of a medicament for the treatment of a condition associated with BTK.

A further aspect of the invention provides a method for inhibiting BTK in a subject, the method comprising administering to the subject a complex as defined above.

An additional aspect of the invention provides a method of treating a disease, disorder or condition associated with BTK in a subject, the method comprising administering to the subject an effective amount of a complex as defined above.

Another aspect of the invention provides a method of treating a disease, disorder or condition in a subject, the method comprising administering to the subject an effective amount of a complex as defined above, wherein the disease, disorder or condition is selected from Type I hypersensitivity reactions, autoimmune diseases, inflammatory disorders, cancer, and non-malignant proliferative disorders.

A further aspect of the invention provides a method of treating a disease, disorder or condition in a subject, the method comprising administering to the subject an effective amount of a complex as defined above, wherein the disease, disorder or condition is selected from allergic rhinitis, asthma, atopic dermatitis, rheumatoid arthritis, multiple sclerosis, systemic lupus erythematosus, lupus nephritis, psoriasis, immune thrombocytopenic purpura, inflammatory bowel disease, chronic obstructive pulmonary disease, Sjögren's syndrome, ankylosing spondylitis, Behcet's disease, pemphigus vulgaris, idiopathic plasmacytic lymphadenopathy, atherosclerosis, myocardial infarction, and thrombosis.

An additional aspect of the invention provides a method of treating a disease, disorder or condition in a subject, the method comprising administering to the subject an effective amount of a complex as defined above, wherein the disease, disorder or condition is selected from B-cell lymphoma, chronic lymphocytic leukemia, and multiple myeloma.

Another aspect of the invention provides a combination of an effective amount of a complex as defined above, and at least one additional pharmacologically active agent.

DETAILED DESCRIPTION OF THE INVENTION

Figure 1:
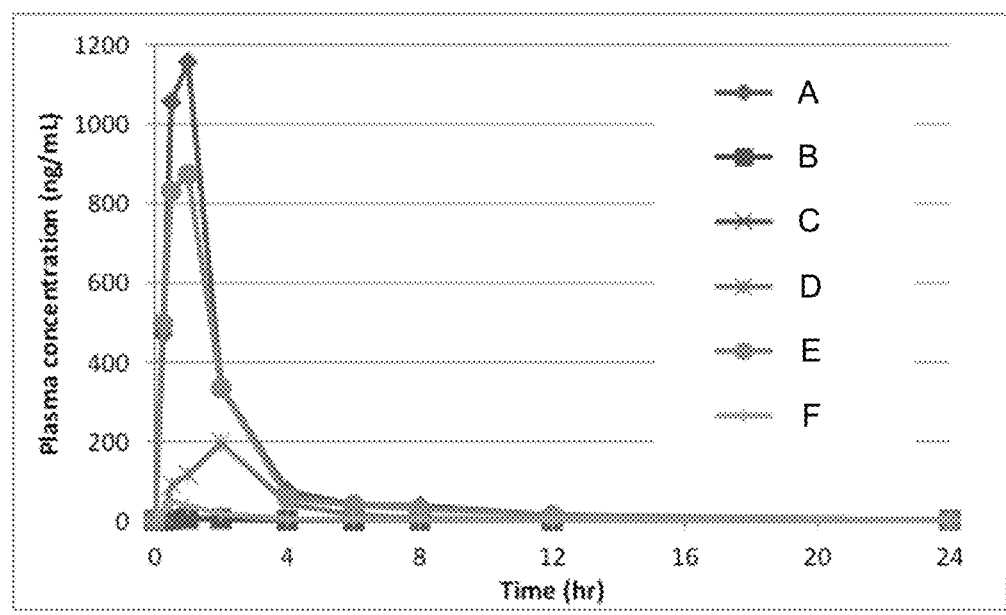
FIG. 1 shows the mean concentration of the compound of Example 1 in blood as a function of time following oral dosing of dogs with Formulations A, B, C, D, E, and F.

Unless otherwise indicated, this disclosure uses definitions provided below.

"About" or "approximately," when used in connection with a measurable numerical variable, refers to the indicated value of the variable and to all values of the variable that are within the experimental error of the indicated value or within 10 percent of the indicated value, whichever is greater.

"Condition associated with BTK" and similar phrases relate to a disease, disorder or condition in a subject for which inhibition of BTK may provide a therapeutic or prophylactic benefit.

"Drug," "drug substance," "active pharmaceutical ingredient," and the like, refer to a compound (e.g., compound of Formula 1) that may be used for treating a subject in need of treatment.

"Drug product," "pharmaceutical dosage form," "dosage form," "final dosage form" and the like, refer to a pharmaceutical composition suitable for treating a subject in need of treatment and generally may be in the form of tablets, capsules, sachets containing powder or granules, patches, films, and the like.

"Effective amount" of a drug, "therapeutically effective amount" of a drug, and the like, refer to the quantity of the drug that may be used for treating a subject and may depend on the weight and age of the subject and the route of administration, among other things.

"Excipient" refers to any diluent or vehicle for a drug.

"Opposite enantiomer" refers to a molecule that is a non-superimposable mirror image of a reference molecule, which may be obtained by inverting all of the stereogenic centers of the reference molecule. For example, if the reference molecule has S absolute stereochemical configuration, then the opposite enantiomer has R absolute stereochemical configuration. Likewise, if the reference molecule has S,S absolute stereochemical configuration, then the opposite enantiomer has R,R stereochemical configuration, and so on.

"Pharmaceutical composition" refers to the combination of one or more drug substances and one or more excipients.

"Pharmaceutically acceptable" substances refer to those substances which are suitable for administration to subjects.

"Pure stereoisomer" and variants thereof refer to a sample containing a compound which has a specific stereochemical configuration and which comprises at least about 99.5% of the sample.

"Stereoisomer" and "stereoisomers" of a compound with given stereochemical configuration refer to the opposite enantiomer of the compound and to any diastereoisomers, including geometrical isomers (Z/E) of the compound. For example, if a compound has S,R,Z stereochemical configuration, its stereoisomers would include its opposite enantiomer having R,S,Z configuration, and its diastereomers having S,S,Z configuration, R,R,Z configuration, S,R,E configuration, R,S,E configuration, S,S,E configuration, and R,R,E configuration. If the stereochemical configuration of a compound is not specified, then "stereoisomer" refers to any one of the possible stereochemical configurations of the compound.

"Substantially pure stereoisomer" and variants thereof refer to a sample containing a compound having a specific stereochemical configuration and which comprises at least about 95% of the sample.

"Subject" refers to a mammal, including a human.

"Substituted," when used in connection with a chemical substituent or moiety (e.g., a $C_{1-6}$ alkyl group), means that one or more hydrogen atoms of the substituent or moiety have been replaced with one or more non-hydrogen atoms or groups, provided that valence requirements are met and that a chemically stable compound results from the substitution.

"Treating" refers to reversing, alleviating, inhibiting the progress of, or preventing a disease, disorder or condition to which such term applies, or to reversing, alleviating, inhibiting the progress of, or preventing one or more symptoms of such disorder, disease or condition.

"Treatment" refers to the act of "treating," as defined immediately above.

The following abbreviations may be used in the specification: Ac (acetyl); ACN (acetonitrile); AIBN (azo-bis-isobutyronitrile); API (active pharmaceutical ingredient); aq (aqueous); Boc (tert-butoxycarbonyl); Cbz (carbobenzyloxy); CDI (1,1'-carbonyldiimidazole); dba (dibenzylideneacetone); DBU (1,8-diazabicyclo[5.4.0]undec-1(7)-ene); DCC (1,3-dicyclohexylcarbodiimide); DCM (dichloromethane); DIPEA (N,N-diisopropylethylamine, Hünig's Base); DMA (N,N-dimethylacetamide); DMAP (4-dimethylaminopyridine); DMARD (disease modifying antirheumatic drug); DME (1,2-dimethoxyethane); DMF (N,N-dimethylformamide); DMSO (dimethylsulfoxide); DPPA (diphenylphosphoryl azide); dppf (1,1'-bis(diphenylphosphino)ferrocene); DTT (dithiothreitol); EDA ethoxylated dodecyl alcohol, Brj®35); EDC (N-(3-dimethylaminopropyl)-N'-ethylcarbodiimide); EDTA (ethylenediaminetetraacetic acid); ee (enantiomeric excess); eq (equivalents); Et (ethyl); Et$_3$N (triethylamine); EtOAc (ethyl acetate); EtOH (ethanol); 5-FAM (5-carboxyfluorescein); HATU (2-(3H-[1,2,3]triazolo[4,5-b]pyridin-3-yl)-1,1,3,3-tetramethyluronium hexafluorophosphate(V)); HEPES (4-(2-hydroxyethyl)piperazine-1-ethanesulfonic acid); HOAc (acetic acid); HOBt (1H-benzo[d][1,2,3]triazol-1-ol); IC$_{50}$ (concentration at 50% inhibition); IPA (isopropanol); IPAc (isopropyl acetate); IPE (isopropylether); LDA (lithium diisopropylamide); LiHMDS (lithium bis(trimethylsilyl)amide); mCPBA (m-chloroperoxybenzoic acid); Me (methyl); MeOH (methanol); MTBE (methyl tert-butyl ether); mp (melting point); NaOt-Bu (sodium tertiary butoxide); NMN (N-methylmorpholine); NMP (1-methyl-2-pyrrolidinone); PE (petroleum ether); Ph (phenyl); pIC$_{50}$ (-log$_{10}$(IC$_{50}$), where IC$_{50}$ is given in molar (M) units); Pr (propyl); i-Pr (isopropyl); PTFE (polytetrafluoroethylene); RT (room temperature, approximately 20° C. to 25° C.); TCEP (tris(2-carboxyethyl)phosphine); Tf (trifluoromethylsulfonyl); TFA (trifluoroacetic acid); TFAA (2,2,2-trifluoroacetic anhydride); THF (tetrahydrofuran); TMS (trimethylsilyl); and Tris buffer (2-amino-2-hydroxymethylpropane-1,3-diol buffer).

This disclosure describes a complex of a compound of Formula 1, a stereoisomer thereof, or a tautomer of the compound of Formula 1 or stereoisomer thereof, and a cyclodextrin. The complex is an amorphous solid which exhibits improved aqueous solubility and bioavailability over the corresponding crystalline form of the compound. This disclosure also concerns materials and methods for preparing the complex, pharmaceutical compositions which contain the complex, and the use of the complex to treat diseases, disorders, and conditions associated with BTK, including Type I hypersensitivity reactions, autoimmune diseases, inflammatory disorders, cancer, non-malignant proliferative disorders, and other diseases, disorders or conditions associated with BTK.

As used in this disclosure, "cyclodextrin" refers to cyclic oligosaccharides consisting of (α-1,4)-linked α-D-glucopyranose units. Each subunit of a naturally-occurring (unmodified or parent) cyclodextrin has secondary hydroxy groups at the 2- and 3-positions and a primary hydroxy group at the 6-position. A cyclodextrin may be thought of as a toroid or hollow truncated cone, which because of the location of the hydroxy groups has a hydrophilic exterior surface and a comparatively less lipophilic internal cavity. The internal cavity may capture at least a portion of a drug molecule, such as the compound of Formula 1, which results in the formation of an inclusion complex. Covalent bonds are neither made nor broken during the formation of the drug-cyclodextrin complex. In aqueous solution, the complex dissociates, resulting in free drug molecules in equilibrium with drug molecules bound in the cyclodextrin cavities. Unless stated otherwise, cyclodextrin refers to both unmodified cyclodextrins and to chemically-modified cyclodextrins, i.e., a "cyclodextrin derivative."

"Cyclodextrin derivative" refers to a structural analog of a parent cyclodextrin in which one or more of the 2-hydroxy, 3-hydroxy, and 6-hydroxy groups in the α-D-glucopyranose subunits are chemically modified,

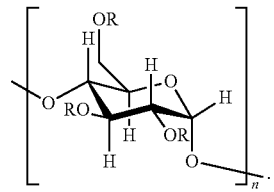

A

For naturally-occurring cyclodextrins, each R in Formula A is hydrogen, whereas for cyclodextrin derivatives, at least one R is non-H. For both naturally-occurring and chemically modified cyclodextrins, α-cyclodextrin, β-cyclodextrin, and γ-cyclodextrin correspond to n being 6, 7, and 8 in Formula A, respectively.

Table 1 lists exemplary cyclodextrins and corresponding values of R in Formula A. Exemplary cyclodextrins include naturally-occurring α-, β-, and γ-cyclodextrins, as well as α-, β-, and γ-cyclodextrin derivatives such as (2-hydroxypropyl)-β-cyclodextrin, randomly methylated β-cyclodextrin, sulfobutylether β-cyclodextrin, and (2-hydroxypropyl)-γ-cyclodextrin. Other useful cyclodextrin derivatives include methyl-, dimethyl-, and trimethyl-β-cyclodextrin (tri-O-methyl-β-cyclodextrin); randomly dimethylated-β-cyclodextrin; ethyl-, diethyl-, and triethyl-β-cyclodextrin (tri-O-ethyl-β-cyclodextrin); (2-hydroxyethyl)-β-cyclodextrin and (3-hydroxypropyl)-β-cyclodextrin; (2,3-dihydroxypropyl)-β-cyclodextrin and (2-hydroxyisobutyl)-β-cyclodextrin; carboxymethyl-β-cyclodextrin and carboxymethyl ethyl-β-cyclodextrin; tributyryl-β-cyclodextrin (tri-O-butyryl-β-cyclodextrin), trivaleryl-β-cyclodextrin (tri-O-valeryl-β-cyclodextrin), and dihexanoyl-β-cyclodextrin (di-O-hexanoyl-β-cyclodextrin); glucosyl-β-cyclodextrin (6-O-α-D-glucosyl-β-cyclodextrin) and maltosyl-β-cyclodextrin (6-O-α-maltosyl-β-cyclodextrin). For a discussion of cyclodextrin in drug products, see M. E. Davis and M. E. Brewster, *Nat. Rev. Drug Disc.* 3(12):1023-1035 (2004); see also R. C. et al., *AAPS Pharm Sci Tech* 6(2):329-357 (2005).

TABLE 1

| Cyclodextrins | |
| --- | --- |
| Name | R in Formula A |
| α-cyclodextrin (unmodified) | H |
| β-cyclodextrin (unmodified) | H |
| γ-cyclodextrin (unmodified) | H |
| methyl-β-cyclodextrin | —CH$_3$ or —H |
| dimethyl-β-cyclodextrin | —CH$_3$ or —H |
| trimethyl-β-cyclodextrin | —CH$_3$ |
| randomly methylated-β-cyclodextrin | —CH$_3$ or —H |
| randomly dimethylated-β-cyclodextrin | —CH$_3$ or —H |
| ethyl-β-cyclodextrin | —CH$_2$CH$_3$ or —H |
| diethyl-β-cyclodextrin | —CH$_2$CH$_3$ or —H |
| triethyl-β-cyclodextrin | —CH$_2$CH$_3$ |
| (2-hydroxyethyl)-β-cyclodextrin | —CH$_2$CH$_2$OH or —H |
| (2-hydroxypropyl)-β-cyclodextrin | —CH$_2$CHOHCH$_3$ or —H |
| (2-hydroxypropyl)-γ-cyclodextrin | —CH$_2$CHOHCH$_3$ or —H |
| (3-hydroxypropyl)-β-cyclodextrin | —(CH$_2$)$_3$OH or —H |
| (2,3-dihydroxypropyl)-β-cyclodextrin | —CH$_2$CHOHCH$_2$OH or —H |
| (2-hydroxyisobutyl)-β-cyclodextrin | —CH$_2$C(CH$_3$)$_2$OH or —H |
| carboxymethyl-β-cyclodextrin | —CH$_2$C(O)O$^-$M$^+$ or —H |
| carboxymethyl ethyl-β-cyclodextrin | —CH$_2$C(O)O$^-$M$^+$, —CH$_2$CH$_3$ or —H |
| tributyryl-β-cyclodextrin | —C(O)(CH$_2$)$_2$CH$_3$ |
| trivaleryl-β-cyclodextrin | —C(O)(CH$_2$)$_3$CH$_3$ |

TABLE 1-continued

Cyclodextrins

| Name | R in Formula A |
|---|---|
| dihexanoyl-β-cyclodextrin | —C(O)(CH$_2$)$_4$CH$_3$ or —H |
| sulfobutylether-β-cyclodextrin | —(CH$_2$)$_4$SO$_3^-$M$^+$ or —H |
| glucosyl-β-cyclodextrin | -glucosyl or —H |
| maltosyl-β-cyclodextrin | -maltosyl or —H |

In Table 1, M$^+$ represents a pharmaceutically acceptable cationic species, which includes H$^+$, Li$^+$, Na$^+$, K$^+$, and NH$_4^+$, among others. Thus, for example, carboxymethyl-β-cyclodextrin and carboxymethyl ethyl-β-cyclodextrin may include at least one R which is —CH$_2$C(O)O$^-$Na$^+$, and sulfobutylether β-cyclodextrin may include at least one R which is —(CH$_2$)$_4$SO$_3^-$Na$^+$.

The compound of Formula 1, a stereoisomer thereof, or a tautomer of the compound of Formula 1 or stereoisomer thereof, may form inclusion complexes with any one of the cyclodextrins listed in Table 1, including, for example, naturally-occurring β-cyclodextrin and γ-cyclodextrin, chemically modified β-cyclodextrin derivatives (2-hydroxypropyl)-β-cyclodextrin, methyl β-cyclodextrin, and sulfobutylether β-cyclodextrin, and chemically modified γ-cyclodextrin derivative (2-hydroxypropyl)-γ-cyclodextrin. Naturally-occurring (unmodified) β-cyclodextrin and γ-cyclodextrin are commercially available from Wacker Chemie AG under the trade names CAVAMAX® W7 PHARMA and CAVAMAX® W8 PHARMA. Likewise chemically modified cyclodextrin derivatives (2-hydroxypropyl)-β-cyclodextrin, (2-hydroxypropyl)-γ-cyclodextrin, and methyl β-cyclodextrin are available under the trade names CAVASOL® W7 HP PHARMA, CAVASOL® W8 HP PHARMA, and CAVASOL® W7 M PHARMA, respectively. CAVASOL® W7 HP PHARMA has a chemical structure according to Formula A in which n is 7 and R is (—CH$_2$CHOHCH$_3$)$_t$ or (—H)$_{21-t}$ and t is about 4.1 to about 5.1; CAVASOL® W8 HP PHARMA has a chemical structure according to Formula A in which n is 8 and R is (—CH$_2$CHOHCH$_3$)$_t$ or (—H)$_{24-t}$ and t is about 4 to about 5.6; and CAVASOL® W7 M PHARMA has a chemical structure in which n is 7 and R is (—CH$_3$)$_t$ or (—H)$_{21-t}$ and t is about 11 to about 14. Useful sulfobutylether β-cyclodextrins are commercially available from CyDex Pharmaceuticals, Inc. under the trade name CAPTISOL®, which has a chemical structure according to Formula A in which n is 7 and R is (—(CH$_2$)$_4$SO$_3^-$Na$^+$)$_t$ or (—H)$_{21-t}$ and t is about 6 to about 7.1.

The complex is an amorphous solid. The term "amorphous" refers to a state in which the material lacks long range order at the molecular level and, depending upon temperature, may exhibit the physical properties of a solid or a liquid. Typically such materials do not give distinctive X-ray diffraction patterns and, while exhibiting the properties of a solid, are more formally described as a liquid. Upon heating, a change from solid to liquid properties occurs which is characterized by a change of state, typically second order ("glass transition"). The term "crystalline" refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterized by a phase change, typically first order ("melting point").

The compound of Formula 1 may exist as polymorphs, stereoisomers, tautomers, or some combination thereof, and may be isotopically-labeled.

The compound of Formula 1 may exist as stereoisomer (S)-3-(1-((1-acryloylpyrrolidin-3-yl)oxy)isoquinolin-3-yl)-1H-1,2,4-triazol-5(4H)-one,

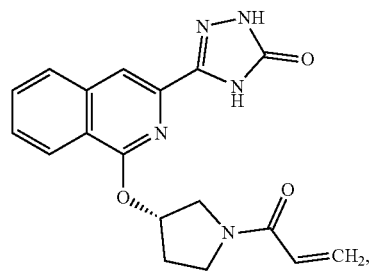 [SMILES: C=CC(=O)N1CC[C@H](Oc2nc(-c3n[nH]c(=O)[nH]3)cc3ccccc23)C1]

or as stereoisomer (R)-3-(1-((1-acryloylpyrrolidin-3-yl)oxy)isoquinolin-3-yl)-1H-1,2,4-triazol-5(4H)-one,

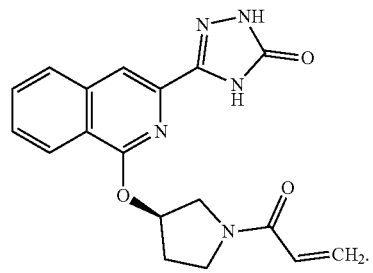 [SMILES: C=CC(=O)N1CC[C@@H](Oc2nc(-c3n[nH]c(=O)[nH]3)cc3ccccc23)C1]

The stereoisomers (i.e., the enantiomer and its opposite enantiomer) may be pure, substantially pure, or a mixture.

The compound of Formula 1 or stereoisomer thereof may exist as tautomers, which are isomers resulting from tautomerization, including imine-enamine, keto-enol, oxime-nitroso, and amide-imidic acid tautomerism. The triazolone moiety of Formula 1 may exist, for example, in the following tautomeric forms:

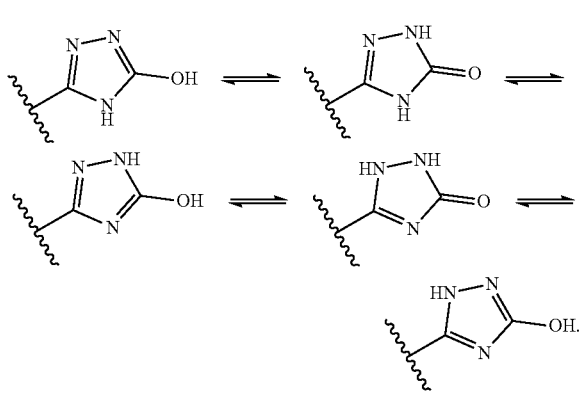

The compound of Formula 1 may exhibit more than one type of isomerism.

The compound of Formula 1, stereoisomer thereof, or tautomer of the compound of Formula 1 or stereoisomer thereof, may possess isotopic variations, in which at least one atom is replaced by an atom having the same atomic number, but an atomic mass different from the atomic mass usually found in nature. Isotopes suitable for inclusion in compounds of Formula 1 include, for example, isotopes of hydrogen, such as $^2$H and $^3$H; isotopes of carbon, such as $^{11}$C, $^{13}$C and $^{14}$C; isotopes of nitrogen, such as $^{13}$N and $^{15}$N; and isotopes of oxygen, such as $^{15}$O, $^{17}$O and $^{18}$O. Use of isotopic variations (e.g., deuterium, $^2$H) may afford certain therapeutic advantages resulting from greater metabolic stability, for example, increased in vivo half-life or reduced dosage requirements. Additionally, certain isotopic variations of the disclosed compounds may incorporate a radioactive isotope (e.g., tritium, $^3$H, or $^{14}$C), which may be useful in drug and/or substrate tissue distribution studies. Substitution with positron emitting isotopes, such as $^{11}$C, $^{15}$O and $^{13}$N, may be useful in Positron Emission Topography (PET) studies for examining substrate receptor occupancy. Isotopically-labeled compounds may be prepared by processes analogous to those described elsewhere in the disclosure using an appropriate isotopically-labeled reagent in place of a non-labeled reagent.

The complex may be prepared from the compound of Formula 1 or from a stereoisomer thereof, or from a tautomer of the compound of Formula 1 or stereoisomer thereof, by spray drying, lyophilization, and other methods. Spray drying involves dissolving the compound and cyclodextrin in one or more compatible solvents, atomizing the resulting solution, and evaporating the solvent or solvents to form the complex. Lyophilization or freeze drying also involves dissolving the compound and cyclodextrin in a compatible solvent (usually water), rapidly freezing the solution, and removing the solvent via sublimation (typically under vacuum) and desorption. For more detailed description of lyophilization, see Georg-Wilhelm Oetjen, "Freeze-Drying," *Ullmann's Encyclopedia of Industrial Chemistry* (2004).

For each of these methods, the fraction of drug substance that is amorphous is in the range of about 50% w/w to about 100% w/w, from about 75% w/w to about 100% w/w, from about 90% w/w to about 100% w/w, or from about 95% w/w to about 100% w/w, based on the total mass of the compound of Formula 1. Ideally, the fraction of drug that is amorphous is in the range of about 99% w/w to about 100% w/w, based on the total mass of the compound of Formula 1.

As noted above, the complex may be prepared by spray drying, which includes dissolving the compound of Formula 1 in one or more compatible solvents to form a solution. Generally, a compatible solvent is any liquid which will dissolve the compound of Formula 1 and the cyclodextrin. In practice, a compatible solvent includes any liquid which at room temperature will completely dissolve the compound of Formula 1 and the cyclodextrin at respective concentrations of about 0.5% w/w or greater, about 1% w/w or greater, or more typically, at concentrations of about 5% w/w or greater. Useful solvents include those which are volatile, have a normal boiling point of about 150° C. or less, exhibit relatively low toxicity, and can be removed from the resulting complex such that the level of solvent in the drug product meets the International Committee on Harmonization (ICH) guidelines for residual solvent. Additional processing, such as tray-drying, may be required to meet ICH residual solvent levels.

The complex is advantageously prepared using water as the solvent. Although the compound of Formula 1 is poorly soluble in water at neutral pH and below, its aqueous solubility increases with increasing basicity, so adjusting the pH of water to about 10 or above, to about 11 or above, to about 12 or above, or to about 13 or above, improves aqueous solubility. Thus, the compound of Formula 1 may be first dissolved in an aqueous base, such as NaOH, KOH, and the like, and then mixed with an aqueous cyclodextrin solution. The concentration of the base may range from about $10^{-4}$M to about 1M, from about $10^{-3}$M to about 1M, from about $10^{-2}$M to about 1M, or from about $10^{-1}$M to about 1N. The solution may be prepared by adding the compound of Formula 1 to the aqueous base with concurrent or subsequent mixing, and then adding cyclodextrin with concurrent or subsequent mixing. The cyclodextrin is typically added as an aqueous solution with a concentration of about 1-60% w/v, about 10-50% w/v, about 20-40% w/v, or about 40% w/v). Mixing may be carried out using mechanical means, e.g., through the use of overhead mixers, magnetically driven mixers or stirring bars, planetary mixers, or homogenizers. The pH of the resulting solution may be adjusted to a pH of about 7 and the aqueous solution spray-dried (e.g., lyophilized).

The compound of Formula 1 and cyclodextrin may be added to the aqueous base up to their respective solubility limits, but to ensure complete dissolution, the amount added is usually less than about 80% of the solubility limit at the solution temperature. The concentration of the compound of Formula 1 typically ranges from about 0.1% w/w to about 10% w/w depending on its solubility, and the concentration of cyclodextrin typically ranges from about 0.1% w/w to about 20% w/w. The concentration of the compound of Formula 1 in the solution is typically at least about 0.1%, 0.5%, 1%, or 5% w/w, and the amount of cyclodextrin is typically about 1 to about 20 times the amount of active compound based on molar concentration. Although increasing the concentration of the active compound and cyclodextrin reduces the volume of solvent, higher concentrations of the active agent and cyclodextrin may be too viscous to atomize efficiently into small droplets. A solution viscosity of about 0.5 cp to about 50,000 cp or about 10 cp to about 2,000 cp generally results in satisfactory atomization.

The solution comprising the compound of Formula 1, cyclodextrin, and solvent (usually water) is delivered to an atomizer that breaks the solution into small droplets. Useful atomizers include "pressure" or single-fluid nozzles; two-fluid nozzles; centrifugal or spinning-disk atomizers; ultrasonic nozzles; and mechanical vibrating nozzles. Detailed descriptions of atomization processes can be found in Lefebvre, *Atomization and Sprays* (1989), and in *Perry's Chemical Engineers' Handbook* (7th ed. 1997). Generally, the droplets produced by the atomizer are less than about 500 μm in diameter when they exit the atomizer.

Once atomized, at least a portion of the solvent (e.g., water) is removed from the solution to produce a plurality of solid particles comprising the complex. The amount of solvent removed to form solid particles depends on the solubility of the complex in the solvent and the concentration of complex in the solution prior to atomization. Generally at least about 60% w/w of the solvent originally present in the solution is removed to form solid particles. The greater the amount of solvent removed from the solution, the less likely crystalline compound is formed. Thus, the amount of solvent removed from the solution to form the amorphous complex is typically at least 70% w/w, at least 80% w/w, or at least 90% w/w.

Atomization and solvent removal occur in a chamber where process conditions may be controlled. The driving force for solvent removal is generally provided by maintaining the partial pressure of the solvent in the chamber below the vapor pressure of the solvent at the temperature of the drying droplets. This may be accomplished by maintaining a partial vacuum in the chamber (e.g., total pressure of about 0.01 atmospheres to about 0.50 atmospheres), by mixing the liquid droplets with a warm drying gas, or both. Some of the energy required for evaporation of solvent may be provided by heating the solution prior to atomization, though generally the energy comes primarily from the drying gas. The solution temperature may range from just above the solvent's freezing point to about 20° C. or more above its normal boiling point, which is achieved by pressurizing the solution. Solution flow rates through the atomizer may vary depending on the type of nozzle, the size of the chamber, and the drying conditions, which include the inlet temperature and the flow rate of the drying gas through the chamber.

The drying gas may, in principle, be essentially any gas, but for safety reasons and to minimize undesirable oxidation of the complex, the process may employ an inert gas such as nitrogen, nitrogen-enriched air or argon. The drying gas is generally introduced into the chamber at a temperature of about 60° C. to about 240° C.

The large surface-to-volume ratio of the droplets and the large driving force for evaporation of solvent leads to rapid solidification times for the droplets. Solidification times of about 20 seconds or less, of about 10 seconds or less, or of about 1 second or less are typical. Rapid solidification helps maintain uniformity and homogeneity of the amorphous complex within and among particles.

The solid particles may remain in the chamber for about 5 seconds to about 60 seconds following solidification, during which time additional solvent evaporates from the particles. Generally, the solvent level of the complex as it exits the chamber is less than about 10% w/w and is often less than 2% w/w. Following formation, the complex may be dried to remove residual solvent using a suitable process, including tray drying, fluid bed drying, microwave drying, belt drying, rotary drying, or vacuum drying. After drying, residual solvent level is typically less than about 1% w/w and is often less than about 0.1% w/w.

The resulting spray-dried complex is usually in the form of small particles. The mean (volume) diameter of the particles may be less than about 1000 µm, less than about 500 µm, less than about 100 µm, less than about 50 µm, or less than about 25 µm. The size of the particles may be determined by sieve analysis, microscopy, light scattering, or sedimentation. Useful equipment for measuring particle size includes Coulter Counters, Malvern Particle Size Analyzers, and the like. See, e.g., A. R. Gennaro (ed.), *Remington: The Science and Practice of Pharmacy* (20th ed., 2000).

For a general description of spray-drying processes and spray-drying equipment, see *Perry's Chemical Engineers' Handbook*, pages 20-54 to 20-57 (6th ed., 1984). Further details of spray drying processes and equipment may be found in Marshall, "Atomization and Spray-Drying," *Chem. Eng. Prog. Monogr. Series* 2, 50 (1954); see also, Masters, *Spray Drying Handbook* (4th ed., 1985) and U.S. Pat. No. 6,763,607.

The complex of the compound of Formula 1, stereoisomer thereof, or tautomer of the compound of Formula 1 or stereoisomer thereof, may be administered alone or in combination with one or more pharmacologically active compounds. Generally, one or more these compounds are administered as a pharmaceutical composition (a formulation) in association with one or more pharmaceutically acceptable excipients. The choice of excipients depends on the particular mode of administration, the effect of the excipient on solubility and stability, and the nature of the dosage form, among other things. Useful pharmaceutical compositions and methods for their preparation may be found, for example, in A. R. Gennaro (ed.), *Remington: The Science and Practice of Pharmacy* (20th ed., 2000).

The complex may be administered orally. Oral administration may involve swallowing in which case the compound enters the bloodstream via the gastrointestinal tract. Alternatively or additionally, oral administration may involve mucosal administration (e.g., buccal, sublingual, supralingual administration) such that the compound enters the bloodstream through the oral mucosa.

Formulations suitable for oral administration include solid and semi-solid systems such as tablets; soft or hard capsules containing multi- or nano-particulates or powders; lozenges; chews; gels; fast dispersing dosage forms; films; and buccal or mucoadhesive patches.

The complex may also be used in fast-dissolving, fast-disintegrating dosage forms such as those described in Liang and Chen, *Expert Opinion in Therapeutic Patents* (2001) 11(6):981-986.

For tablet dosage forms, depending on dose, the active pharmaceutical ingredient (API) may comprise from about 1 wt % to about 80 wt % of the dosage form or more typically from about 5 wt % to about 60 wt % of the dosage form. In addition to the API, tablets may include one or more disintegrants, binders, diluents, surfactants, glidants, lubricants, anti-oxidants, colorants, flavoring agents, preservatives, and taste-masking agents. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, $C_{1-6}$ alkyl-substituted hydroxypropylcellulose, starch, pregelatinized starch, and sodium alginate. Generally, the disintegrant will comprise from about 1 wt % to about 25 wt % or from about 5 wt % to about 20 wt % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinized starch, hydroxypropylcellulose and hydroxypropylmethylcellulose. Tablets may also contain diluents, such as lactose (monohydrate, spray-dried monohydrate, anhydrous), mannitol, xylitol, dextrose, sucrose, sorbitol, microcrystalline cellulose, starch and dibasic calcium phosphate dihydrate.

Tablets may also include surface active agents, such as sodium lauryl sulfate and polysorbate 80, and glidants such as silicon dioxide and talc. When present, surface active agents may comprise from about 0.2 wt % to about 5 wt % of the tablet, and glidants may comprise from about 0.2 wt % to about 1 wt % of the tablet.

Tablets may also contain lubricants such as magnesium stearate, calcium stearate, zinc stearate, sodium stearyl fumarate, and mixtures of magnesium stearate with sodium lauryl sulfate. Lubricants may comprise from about 0.25 wt % to about 10 wt % or from about 0.5 wt % to about 3 wt % of the tablet.

Tablet blends may be compressed directly or by roller compaction to form tablets. Tablet blends or portions of blends may alternatively be wet-, dry-, or melt-granulated, melt congealed, or extruded before tableting. If desired, prior to blending one or more of the components may be sized by screening or milling or both. The final dosage form may comprise one or more layers and may be coated, uncoated, or encapsulated. Exemplary tablets may contain up to about 80 wt % of API, from about 10 wt % to about 90 wt % of binder, from about 0 wt % to about 85 wt % of diluent, from about 2 wt % to about 10 wt % of disintegrant, and from about 0.25 wt % to about 10 wt % of lubricant. For a discussion of blending, granulation, milling, screening, tableting, coating, as well as a description of alternative techniques for preparing drug products, see A. R. Gennaro (ed.), *Remington: The Science and Practice of Pharmacy* (20th ed., 2000); H. A. Lieberman et al. (ed.), *Pharmaceutical Dosage Forms: Tablets*, Vol. 1-3 (2d ed., 1990); and D. K. Parikh & C. K. Parikh, *Handbook of Pharmaceutical Granulation Technology*, Vol. 81 (1997).

Consumable oral films for human or veterinary use are pliable water-soluble or water-swellable thin film dosage forms which may be rapidly dissolving or mucoadhesive. In addition to the API, a typical film includes one or more film-forming polymers, binders, humectants, plasticizers, stabilizers or emulsifiers, viscosity-modifying agents, and solvents. Other film ingredients may include anti-oxidants, colorants, flavorants and flavor enhancers, preservatives, salivary stimulating agents, cooling agents, co-solvents (including oils), emollients, bulking agents, anti-foaming agents, surfactants, and taste-masking agents. Some components of the formulation may perform more than one function.

In addition to dosing requirements, the amount of API in the film may depend on its solubility. If water soluble, the API would typically comprise from about 1 wt % to about 80 wt % of the non-solvent components (solutes) in the film or from about 20 wt % to about 50 wt % of the solutes in the film. A less soluble API may comprise a greater proportion of the composition, typically up to about 88 wt % of the non-solvent components in the film.

The film-forming polymer may be selected from natural polysaccharides, proteins, or synthetic hydrocolloids and typically comprises from about 0.01 wt % to about 99 wt % or from about 30 wt % to about 80 wt % of the film.

Film dosage forms are typically prepared by evaporative drying of thin aqueous films coated onto a peelable backing support or paper, which may carried out in a drying oven or tunnel (e.g., in a combined coating-drying apparatus), in lyophilization equipment, or in a vacuum oven.

Useful solid formulations for oral administration may include immediate release formulations and modified release formulations. Modified release formulations include delayed-, sustained-, pulsed-, controlled-, targeted-, and programmed-release. For a general description of suitable modified release formulations, see U.S. Pat. No. 6,106,864. For details of other useful release technologies, such as high energy dispersions and osmotic and coated particles, see Verma et al, *Pharmaceutical Technology On-line* (2001) 25(2):1-14.

As noted above, the complex may be combined with one or more other pharmaceutically active compounds to treat various diseases, disorders or conditions. In such cases, the active compounds may be combined in a single dosage form as described above or may be provided in the form of a kit which is suitable for co-administration of the compositions. The kit comprises (1) two or more different pharmaceutical compositions, at least one of which contains the complex of the compound of Formula 1 or tautomer thereof; and (2) a device for separately retaining the two pharmaceutical compositions, such as a divided bottle or a divided foil packet. An example of such a kit is the familiar blister pack used for the packaging of tablets or capsules. The kit is suitable for administering different types of dosage forms (e.g., oral and parenteral) or for administering different pharmaceutical compositions at separate dosing intervals, or for titrating the different pharmaceutical compositions against one another. To assist with patient compliance, the kit typically comprises directions for administration and may be provided with a memory aid.

For administration to human patients, the total daily dose of the compound of Formula 1, stereoisomer thereof, or tautomer of the compound of Formula 1 or stereoisomer thereof, is typically in the range of about 1 mg to about 3000 mg for oral administration. The total daily dose may be administered in single or divided doses and, at the physician's discretion, may fall outside of the typical ranges given above. Although these dosages are based on an average human subject having a mass of about 60 kg to about 70 kg, the physician will be able to determine the appropriate dose for a patient (e.g., an infant) whose mass falls outside of this weight range.

As noted above, the complex may be used to treat diseases, disorders or conditions for which inhibition of BTK is indicated. Such diseases, disorders or conditions generally relate to any unhealthy or abnormal state in a subject for which the inhibition of BTK provides a therapeutic benefit. More particularly, such diseases, disorders or conditions may involve the immune system and inflammation, including Type I hypersensitivity (allergic) reactions (allergic rhinitis, allergic asthma, and atopic dermatitis); autoimmune diseases (rheumatoid arthritis, multiple sclerosis, systemic lupus erythematosus, psoriasis, lupus nephritis, immune thrombocytopenic purpura, Sjögren's syndrome, ankylosing spondylitis, and Behcet's disease); inflammatory bowel disease; inflammation of the lung (chronic obstructive pulmonary disease), atherosclerosis, thrombosis, and myocardial infarction. The compounds of Formula 1 may also be used to treat diseases, disorders or conditions related to abnormal cell growth, including hematological malignancies, such as acute myeloid leukemia, B-cell chronic lymphocytic leukemia, B-cell lymphoma (e.g., mantle cell lymphoma), T-cell lymphoma (e.g., peripheral T-cell lymphoma), and multiple myeloma, as well as epithelial cancers (i.e., carcinomas), such as lung cancer (small cell lung cancer and non-small cell lung cancer), pancreatic cancer, and colon cancer.

In addition to the hematological malignancies and epithelial cancers noted above, the complex may also be used to treat other types of cancer, including leukemia (chronic myelogenous leukemia and chronic lymphocytic leukemia); breast cancer, genitourinary cancer, skin cancer, bone cancer, prostate cancer, and liver cancer; brain cancer; cancer of the larynx, gall bladder, rectum, parathyroid, thyroid, adrenal, neural tissue, bladder, head, neck, stomach, bronchi, and kidneys; basal cell carcinoma, squamous cell carcinoma, metastatic skin carcinoma, osteosarcoma, Ewing's sarcoma, reticulum cell sarcoma, and Kaposi's sarcoma; myeloma, giant cell tumor, islet cell tumor, acute and chronic lymphocytic and granulocytic tumors, hairy-cell tumor, adenoma, medullary carcinoma, pheochromocytoma, mucosal neuromas, intestinal ganglioneuromas, hyperplastic corneal nerve tumor, marfanoid habitus tumor, Wilms' tumor, seminoma, ovarian tumor, leiomyomater tumor, cervical dysplasia, neuroblastoma, retinoblastoma, myelodysplastic syndrome, rhabdomyosarcoma, astrocytoma, non-Hodgkin's lymphoma, malignant hypercalcemia, polycythermia vera, adenocarcinoma, glioblastoma multiforma, glioma, lymphomas, and malignant melanomas, among others.

In addition to cancer, the complex may also be used to treat other diseases, disorders or conditions related to abnormal cell growth, including non-malignant proliferative diseases such as benign prostatic hypertrophy, restinosis, hyperplasia, synovial proliferation disorder, idiopathic plasmacytic lymphadenopathy, retinopathy or other neovascular disorders of the eye, among others.

The complex may also be used to treat autoimmune diseases, disorders or conditions in addition to those listed above. Such diseases, disorders or conditions include Crohn's disease, dermatomyositis, diabetes mellitus type 1, Goodpasture's syndrome, Graves' disease, Guillain-Barré syndrome, Hashimoto's disease, mixed connective tissue damage, myasthenia gravis, narcolepsy, pemphigus vulgaris, pernicious anemia, polymyositis, primary biliary cirrhosis, temporal arteritis, ulcerative colitis, vasculitis, and Wegener's granulomatosis, among others.

The complex may be used to treat inflammatory diseases, disorders or conditions including asthma, chronic inflammation, chronic prostatitis, glomerulonephritis, hypersensitivities, inflammatory bowel diseases (ulcerative colitis in addition to Crohn's disease), pelvic inflammatory disease, reperfusion injury, transplant rejection, vasculitis, and systemic inflammatory response syndrome.

The complex may also be used to treat specific diseases or conditions that may fall within one or more general disorders described above, including arthritis. In addition to rheumatoid arthritis, Sjögren's syndrome, systemic lupus erythematosus, SLE in children and adolescents, the complex may be used to treat other arthritis diseases, including ankylosing spondylitis, avascular necrosis, Behcet's disease, bursitis, calcium pyrophosphate dihydrate crystal deposition disease (pseudo gout), carpal tunnel syndrome, Ehlers-Danlos syndrome, fibromyalgia, Fifth disease, giant cell arteritis, gout, juvenile dermatomyositis, juvenile rheumatoid arthritis, juvenile spondyloarthropathy, Lyme disease, Marfan syndrome, myositis, osteoarthritis, osteogenesis imperfect, osteoporosis, Paget's disease, psoriatic arthritis, Raynaud's phenomenon, reactive arthritis, reflex sympathetic dystrophy syndrome, scleroderma, spinal stenosis, Still's disease, and tendinitis, among others.

The complex may be combined with one or more pharmacologically active compounds or therapies for the treatment of one or more diseases, disorders or conditions for which BTK is indicated, including those involving the immune system, inflammation, and abnormal cell growth. For example, the complex may be administered simultaneously, sequentially or separately in combination with one or more compounds or therapies for treating arthritis, including rheumatoid arthritis and osteoarthritis, or for treating cancer, including hematological malignancies, such as acute myeloid leukemia, B-cell chronic lymphocytic leukemia, B-cell lymphoma, T-cell lymphoma, multiple myeloma, and carcinomas, such as lung cancer, pancreatic cancer, and colon cancer. Such combinations may offer significant therapeutic advantages, including fewer side effects, improved ability to treat underserved patient populations, or synergistic activity.

For example, when used to treat arthritis, the complex may be combined with one or more nonsteroidal anti-inflammatory drugs (NSAIDs), analgesics, corticosteroids, biological response modifiers, and protein-A immunoadsorption therapy. Alternatively or additionally, when treating rheumatoid arthritis, the complex may be combined with one or more disease modifying antirheumatic drugs (DMARDs), and when treating osteoarthritis, the complex may be combined with one or more osteoporosis agents.

Representative NSAIDs include apazone, aspirin, celecoxib, diclofenac (with and without misoprostol), diflunisal, etodolac, fenoprofen, flurbiprofen, ibuprofen, indomethacin, ketoprofen, meclofenamate sodium, mefenamic acid, meloxicam, nabumetone, naproxen, oxaprozin, phenylbutazone, piroxicam, choline and magnesium salicylates, salsalate, and sulindac. Representative analgesics include acetaminophen and morphine sulfate, as well as codeine, hydrocodone, oxycodone, propoxyphene, and tramadol, all with or without acetaminophen. Representative corticosteroids include betamethasone, cortisone acetate, dexamethasone, hydrocortisone, methylprednisolone, prednisolone, and prednisone. Representative biological response modifiers include TNF-α inhibitors, such as adalimumab, etanercept, and infliximab; selective B-cell inhibitors, such as rituximab; IL-1 inhibitors, such as anakinra, and selective costimulation modulators, such as abatacept.

Representative DMARDs include auranofin (oral gold), azathioprine, chlorambucil, cyclophosamide, cyclosporine, gold sodium thiomalate (injectable gold), hydroxychloroquine, leflunomide, methotrexate, minocycline, mycophenolate mofetil, penicillamine, sulfasalazine, and JAK3 inhibitor (e.g., tofacitinib). Representative osteoporosis agents include bisphosphonates, such as alendronate, ibandronate, risedronate, and zoledronic acid; selective estrogen receptor modulators, such as droloxifene, lasofoxifene, and raloxifene; hormones, such as calcitonin, estrogens, and parathyroid hormone; and immunosuppressant agents such as azathioprine, cyclosporine, and rapamycin.

Particularly useful combinations for treating rheumatoid arthritis include the complex and methotrexate; the complex and one or more biological response modifiers, such as leflunomide, etanercept, adalimumab, and infliximab; or the complex, methotrexate, and one or more biological response modifiers, such as leflunomide, etanercept, adalimumab, and infliximab.

For the treatment of thrombus and restenosis, the complex may be combined with one or more cardiovascular agents such as calcium channel blockers, statins, fibrates, beta-blockers, ACE inhibitors, and platelet aggregation inhibitors.

The complex of the compound of Formula 1, stereoisomer thereof, or tautomer of the compound of Formula 1 or stereoisomer thereof, may also be combined with one or more compounds or therapies for treating cancer. These include chemotherapeutic agents (i.e., cytotoxic or antineoplastic agents) such as alkylating agents, antibiotics, antimetabolic agents, plant-derived agents, and topoisomerase inhibitors, as well as molecularly targeted drugs which block the growth and spread of cancer by interfering with specific molecules involved in tumor growth and progression. Molecularly targeted drugs include both small molecules and biologics.

Representative alkylating agents include bischloroethylamines (nitrogen mustards, e.g., chlorambucil, cyclophosphamide, ifosfamide, mechlorethamine, melphalan, and uracil mustard); aziridines (e.g., thiotepa); alkyl alkane sulfonates (e.g., busulfan); nitrosoureas (e.g., carmustine, lomustine, and streptozocin); nonclassical alkylating agents (e.g., altretamine, dacarbazine, and procarbazine); and platinum compounds (e.g., carboplatin, cisplatin, nedaplatin, oxaliplatin, satraplatin, and triplatin tetranitrate).

Representative antibiotic agents include anthracyclines (e.g., aclarubicin, amrubicin, daunorubicin, doxorubicin, epirubicin, idarubicin, pirarubicin, valrubicin, and zorubicin); anthracenediones (e.g., mitoxantrone and pixantrone); and *Streptomyces* (e.g., actinomycin, bleomycin, dactinomycin, mitomycin C, and plicamycin).

Representative antimetabolic agents include dihydrofolate reductase inhibitors (e.g., aminopterin, methotrexate, and pemetrexed); thymidylate synthase inhibitors (e.g., raltitrexed and pemetrexed); folinic acid (e.g., leucovorin);

adenosine deaminase inhibitors (e.g., pentostatin); halogenated/ribonucleotide reductase inhibitors (e.g., cladribine, clofarabine, and fludarabine); thiopurines (e.g., thioguanine and mercaptopurine); thymidylate synthase inhibitors (e.g., fluorouracil, capecitabine, tegafur, carmofur, and floxuridine); DNA polymerase inhibitors (e.g., cytarabine); ribonucleotide reductase inhibitors (e.g., gemcitabine); hypomethylating agent (e.g., azacitidine and decitabine); and ribonucleotide reductase inhibitor (e.g., hydroxyurea); and an asparagine depleter (e.g., asparaginase)

Representative plant-derived agents include vinca alkaloids (e.g., vincristine, vinblastine, vindesine, vinzolidine, and vinorelbine), podophyllotoxins (e.g., etoposide and teniposide), and taxanes (e.g., docetaxel, larotaxel, ortataxel, paclitaxel, and tesetaxel).

Representative type I topoisomerase inhibitors include camptothecins, such as belotecan, irinotecan, rubitecan, and topotecan. Representative type II topoisomerase inhibitors include amsacrine, etoposide, etoposide phosphate, and teniposide, which are derivatives of epipodophyllotoxins.

Molecularly targeted therapies include biologic agents such as cytokines and other immune-regulating agents. Useful cytokines include interleukin-2 (IL-2, aldesleukin), interleukin 4 (IL-4), interleukin 12 (IL-12), and interferon, which includes more than 23 related subtypes. Other cytokines include granulocyte colony stimulating factor (CSF) (e.g., filgrastim) and granulocyte macrophage colony stimulating factor (GM-CSF or CSF2) (e.g., sargramostim, namilumab). Other immuno-modulating agents include *Bacillus* Calmette-Guerin, levamisole, and octreotide; monoclonal antibodies against tumor antigens, such as trastuzumab and rituximab; and cancer vaccines, which induce an immune response to tumors.

In addition, molecularly targeted drugs that interfere with specific molecules involved in tumor growth and progression include inhibitors of epidermal growth factor (EGF), transforming growth factor-alpha (TGF$_\alpha$), TGF$_\beta$, heregulin, insulin-like growth factor (IGF), fibroblast growth factor (FGF), keratinocyte growth factor (KGF), colony stimulating factor (CSF), erythropoietin (EPO), interleukin-2 (IL-2), nerve growth factor (NGF), platelet-derived growth factor (PDGF), hepatocyte growth factor (HGF), vascular endothelial growth factor (VEGF), angiopoietin, epidermal growth factor receptor (EGFR), human epidermal growth factor receptor 2 (HER2), HER4, insulin-like growth factor 1 receptor (IGF1R), IGF2R, fibroblast growth factor 1 receptor (FGF1R), FGF2R, FGF3R, FGF4R, vascular endothelial growth factor receptor (VEGFR), tyrosine kinase with immunoglobulin-like and epidermal growth factor-like domains 2 (Tie-2), platelet-derived growth factor receptor (PDGFR), Abl, Bcr-Abl, Raf, FMS-like tyrosine kinase 3 (FLT3), c-Kit, Src, protein kinase c (PKC), tropomyosin receptor kinase (Trk), Ret, mammalian target of rapamycin (mTOR), Aurora kinase, polo-like kinase (PLK), mitogen activated protein kinase (MAPK), mesenchymal-epithelial transition factor (c-MET), cyclin-dependent kinase (CDK), Akt, extracellular signal-regulated kinases (ERK), poly (ADP) ribose polymerase (PARP), and the like.

Specific molecularly targeted drugs include selective estrogen receptor modulators, such as tamoxifen, toremifene, fulvestrant, and raloxifene; antiandrogens, such as bicalutamide, nilutamide, megestrol, and flutamide; and aromatase inhibitors, such as exemestane, anastrozole, and letrozole. Other specific molecularly targeted drugs include agents which inhibit signal transduction, such as imatinib, dasatinib, nilotinib, trastuzumab, gefitinib, erlotinib, cetuximab, lapatinib, panitumumab, and temsirolimus; agents that induce apoptosis, such as bortezomib; agents that block angiogenesis, such as bevacizumab, sorafenib, and sunitinib; agents that help the immune system destroy cancer cells, such as rituximab and alemtuzumab; and monoclonal antibodies which deliver toxic molecules to cancer cells, such as gemtuzumab ozogamicin, tositumomab, 131I-tositumomab, and ibritumomab tiuxetan.

Biological Activity

The activity of compound of Formula 1, stereoisomer thereof, or tautomers of the compound as Formula 1 or stereoisomer thereof, as BTK inhibitors may be determined by a variety of methods, including in vitro and in vivo methods. The following in vitro assay measures a test compound's ability to inhibit BTK-mediated phosphorylation of a FAM-labeled substrate, 5-FAM-EEP-LYWSFPAKKK-NH$_2$.

Purified BTK may be obtained as follows (Clone SBVC-1603_9P is used). A cDNA sequence encoding residues 382 to 659 of human BTK is cloned into the vector pSXB4. This construct engineers an in-frame translational fusion with the Glutathione-S-Transferase (GST) protein for use in affinity purification. The fusion protein derived from this construct contains a protease recognition sequence to liberate the BTK from the GST affinity tag. High-titer baculoviral stocks, generated using the Bac-to-Bac® system (Invitrogen), are used to express the recombinant protein in *Spodoptera frugiperda* Sf9 cells in 10 L Wave bags. Recombinant proteins are isolated from cellular extracts by passage over Glutathione Sepharose 4B (GE Healthcare) and the BTK moiety is released from the GST affinity tag by treatment with PreScission protease. The BTK recombinant protein is further purified by size exclusion chromatography (HiLoad 16/60 Superdex 200, GE Healthcare) in a buffer containing 20 mM Hepes (pH 7.4), 50 mM NaCl, 10 mM MgCl$_2$, 0.25 mM TCEP and 0.1 mM EDTA. The purity of the fractions is assessed by SDS PAGE and the peak protein fractions are pooled and concentrated using Amicon Ultra-15 Centrifugal Filter Devices (Millipore).

The inhibitory properties of compounds relative to BTK is determined using a black 384-well-plate format in a buffer which contains 50 mM Hepes, 10 mM NaCl, 10 mM MgCl$_2$, 0.2 mM EDTA, 0.01% Brij35®, 1 mM DTT, and 0.1 mg/mL BSA at pH 7.3. The test compound is prepared in DMSO using 2-fold serial dilutions for 11 data points, which are added to the buffer so that each dilution contains 3% DMSO. To initiate the assay, 5 µL of 3 µM 5FAM-EEP-LYWSFPAKKK-NH$_2$ (in buffer), 5 µL of diluted test compound (3% DMSO in buffer), and 5 µL of 9 nM BTK and 150 µM ATP in buffer are combined in each well. The reaction mixtures are incubated at room temperature for 60 minutes and then quenched by adding 25 µL of 50 mM EDTA. To quantify the fluorescent-labeled substrate and product following reaction, the test plate is loaded on a Caliper LC-3000, which measures percent of conversion by microfluidic-based separation. Corresponding IC$_{50}$ values are calculated by non-linear curve fitting of the compound concentrations and percent of inhibition to the standard IC$_{50}$ equation and reported as pIC$_{50}$, i.e., $-\log(IC_{50})$, where IC$_{50}$ is molar concentration at 50% inhibition.

EXAMPLES

The following examples are intended to be illustrative and non-limiting, and represent specific embodiments of the present invention.

$^1$H Nuclear magnetic resonance (NMR) spectra were obtained for many of the compounds in the following examples. Characteristic chemical shifts (δ) are given in parts-per-million downfield from tetramethylsilane using conventional abbreviations for designation of major peaks, including s (singlet), d (doublet), t (triplet), q (quartet), m (multiplet), and br (broad). The following abbreviations are used for common solvents: CDCl$_3$ (deuterochloroform), DMSO-d$_6$ (deuterodimethylsulfoxide), CD$_3$OD (deuteromethanol), CD$_3$CN (deuteroacetonitrile), and THF-d$_8$ (deuterotetrahydrofuran). The mass spectra (M+H) were recorded using either electrospray ionization (ESI-MS) or atmospheric pressure chemical ionization (APCI-MS).

Where indicated, products of certain preparations and examples are purified by mass-triggered HPLC (Pump: Waters™ 2525; MS: ZQ™; Software: MassLynx™), flash chromatography or preparative thin layer chromatography (TLC). Reverse phase chromatography is typically carried out on a column (e.g., Gemini™ 5 μm C18 110 Å, Axia™, 30×75 mm, 5 μm) under acidic conditions ("acid mode") eluting with ACN and water mobile phases containing 0.035% and 0.05% trifluoroacetic acid (TFA), respectively, or under basic conditions ("basic mode") eluting with water and 20/80 (v/v) water/acetonitrile mobile phases, both containing 10 mM NH$_4$HCO$_3$. Preparative TLC is typically carried out on silica gel 60 F$_{254}$ plates. After isolation by chromatography, the solvent is removed and the product is obtained by drying in a centrifugal evaporator (e.g., Gene-Vac™), rotary evaporator, evacuated flask, etc. Reactions in an inert (e.g., nitrogen) or reactive (e.g., H$_2$) atmosphere are typically carried out at a pressure of about 1 atmosphere (14.7 psi).

Example 1: (S)-3-(1-((1-acryloylpyrrolidin-3-yl)oxy)isoquinolin-3-yl)-1H-1,2,4-triazol-5(4H)-one

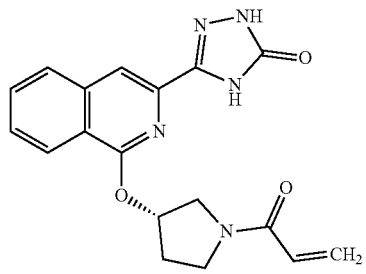 [SMILES: C=CC(=O)N1CC[C@H](Oc2nc(-c3n[nH]c(=O)[nH]3)cc3ccccc23)C1]

Step A: (S)-tert-butyl 3-((3-chloroisoquinolin-1-yl)oxy)pyrrolidine-1-carboxylate

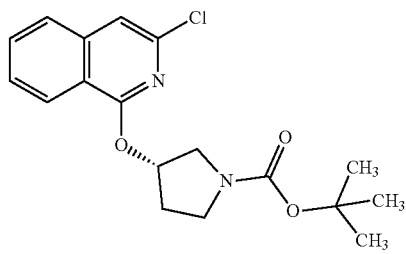 [SMILES: CC(C)(C)OC(=O)N1CC[C@H](Oc2nc(Cl)cc3ccccc23)C1]

To (S)-tert-butyl 3-hydroxypyrrolidine-1-carboxylate (1.134 g, 6.06 mmol) in NMP (10 mL) at 0° C. was added NaH (60%) (202 mg, 5.05 mmol). The mixture was stirred for 5 minutes and 1,3-dichloroisoquinoline (1.000 g, 5.05 mmol) was added. The reaction mixture was stirred at RT for 5 minutes and then heated at 135° C. for 30 minutes in a microwave reactor. The mixture was diluted with water (400 mL) and extracted with EtOAc (3×125 mL). The organic layers were combined, washed with brine, dried over Na$_2$SO$_4$, filtered, and concentrated in vacuo. The crude product was purified by silica column chromatography eluting with a gradient of 25-50% EtOAc in hexane to give the title compound (5.29 g, 75%). $^1$H NMR (500 MHz, DMSO-d$_6$) δ ppm 1.40 (d, J=14.16 Hz, 9H), 2.12-2.34 (m, 2H), 3.42-3.58 (m, 3H), 3.69 (td, J=12.33, 4.64 Hz, 1H), 5.63-5.76 (m, 1H), 7.59 (s, 1H), 7.64 (ddd, J=8.30, 7.08, 1.22 Hz, 1H), 7.81 (td, J=7.57, 1.46 Hz, 1H), 7.87-7.92 (m, 1H), 8.11-8.19 (m, 1H); ESI-MS m/z [M+H-tert-butyl]$^+$ 293.5.

Step B: (S)-tert-butyl 3-((3-cyanoisoquinolin-1-yl)oxy)pyrrolidine-1-carboxylate

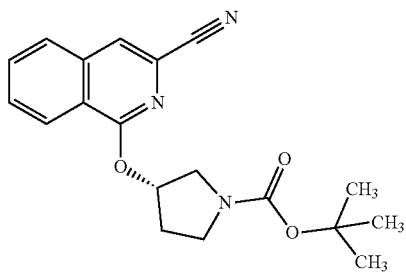 [SMILES: CC(C)(C)OC(=O)N1CC[C@H](Oc2nc(C#N)cc3ccccc23)C1]

A solution of (S)-tert-butyl 3-((3-chloroisoquinolin-1-yl)oxy)pyrrolidine-1-carboxylate (4.430 g, 12.70 mmol), zinc cyanide (2.980 g, 25.40 mmol) and Pd(PPh$_3$)$_4$ (1.468 g, 1.27 mmol) in DMF (36.3 mL) was heated at 160° C. for 20 minutes in a microwave reactor. The reaction mixture was filtered, diluted with water (400 mL) and extracted with EtOAc (2×100 mL). The organic layers were combined, washed with brine, dried over Na$_2$SO$_4$, and concentrated in vacuo. The crude product was purified by silica column chromatography to give the title compound as a white-to-pale-yellow solid (3.570 g, 83%). $^1$H NMR (500 MHz, DMSO-d$_6$) δ ppm 1.40 (d, J=13.18 Hz, 9H), 2.23 (d, J=11.23 Hz, 2H), 3.42-3.59 (m, 3H), 3.65-3.75 (m, 1H), 5.68-5.80 (m, 1H), 7.82-7.89 (m, 1H), 7.91-7.98 (m, 1H), 8.06 (d, J=8.79 Hz, 1H), 8.21-8.30 (m, 2H); ESI-MS m/z [M+H-tert-butyl]$^+$ 284.6.

Step C: (S)-tert-butyl 3-((3-(5-oxo-4,5-dihydro-1H-1,2,4-triazol-3-yl)isoquinolin-1-yl)oxy)pyrrolidine-1-carboxylate

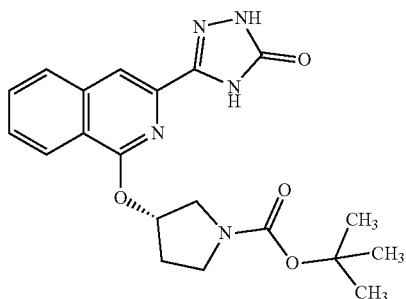

(S)-tert-Butyl 3-((3-cyanoisoquinolin-1-yl)oxy)pyrrolidine-1-carboxylate (4.670 g, 13.76 mmol), ethyl hydrazinecarboxylate (7.160 g, 68.80 mmol), DBU (1.037 mL, 6.88 mmol) and NMP (34.6 mL) were mixed in a 200 mL high pressure reaction vessel. The resulting suspension was heated at 170° C. overnight and was then cooled to room temperature. Crushed ice was added and the mixture was stirred. A yellow precipitate was collected by vacuum filtration, washed with additional water, and dried in a vacuum oven at 45° C. overnight to give the title compound, which was used in the next step without further purification (5.47 g). $^1$H NMR (500 MHz, DMSO-$d_6$) δ ppm 1.33-1.51 (m, 9H), 2.09-2.38 (m, 2H), 3.39-3.60 (m, 3H), 3.75 (dd, J=12.20, 4.88 Hz, 1H), 6.03-6.22 (m, 1H), 7.62-7.71 (m, 1H), 7.81 (td, J=7.57, 1.46 Hz, 1H), 7.95-8.05 (m, 1H), 8.11-8.29 (m, 2H), 11.78 (s, 1H), 12.03 (br s, 1H).

Step D: (S)-3-(1-(pyrrolidin-3-yloxy)isoquinolin-3-yl)-1H-1,2,4-triazol-5(4H)-one

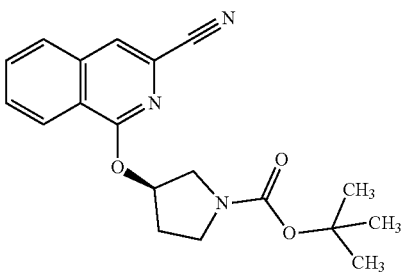

To a 200 mL round-bottom flask charged with crude (S)-tert-butyl 3-((3-(5-oxo-4,5-dihydro-1H-1,2,4-triazol-3-yl)isoquinolin-1-yl)oxy)pyrrolidine-1-carboxylate (5.47 g) and dioxane (27.5 mL) was added 4M HCl in dioxane (13.76 mL, 55.1 mmol). The suspension was stirred at RT with periodic monitoring by HPLC. Upon completion, the reaction mixture was concentrated in vacuo to give an HCl salt of the title compound as a light tan powder that was dried and used without further purification. ESI-MS m/z [M+H]$^+$ 298.6.

Step E: (S)-3-(1-((1-acryloylpyrrolidin-3-yl)oxy)isoquinolin-3-yl)-1H-1,2,4-triazol-5(4H)-one To a suspension of (S)-3-(1-(pyrrolidin-3-yloxy)isoquinolin-3-yl)-1H-1,2,4-triazol-5(4H)-one hydrochloride (4.29 g) in DCM (48.1 mL) was added 2,6-dimethylpyridine (3.19 mL, 27.4 mmol). Upon cooling the suspension to 0° C., acryloyl chloride (1.3 mL, 15.9 mmol) was added drop-wise. The reaction mixture was stirred for 15 minutes and warmed to RT over a period of 90 minutes. Additional 2,6-dimethylpyridine (1.68 mL, 14.43 mmol) and acryloyl chloride (0.469 mL, 5.77 mmol) were added and the mixture was stirred until HPLC indicated the reaction was completed. The product was collected by vacuum filtration, washed with DCM, and dried to give title compound as a pale yellow solid (1.929 g, 39.9% over 3 steps). $^1$H NMR (500 MHz, DMSO-$d_6$) δ ppm 2.16-2.43 (m, 2H), 3.58-3.73 (m, 1H), 3.74-3.91 (m, 2H), 4.10 (dd, J=11.72, 4.88 Hz, 1H), 5.60-5.74 (m, 1H), 6.10-6.25 (m, 2H), 6.53-6.73 (m, 1H), 7.62-7.69 (m, 1H), 7.77-7.85 (m, 1H), 7.95-8.05 (m, 2H), 8.17 (d, J=8.30 Hz, 1H), 11.78 (s, 1H), 12.03 (d, J=13.18 Hz, 1H); ESI-MS m/z [M+H]$^+$ 352.6.

Example 2: (R)-3-(1-((1-acryloylpyrrolidin-3-yl)oxy)isoquinolin-3-yl)-1H-1,2,4-triazol-5(4H)-one

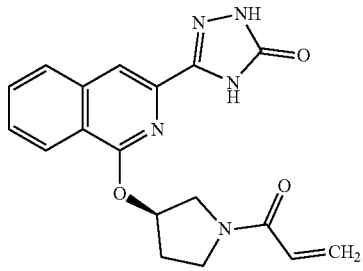 [SMILES: C=CC(=O)N1CC[C@@H](Oc2nc(-c3n[nH]c(=O)[nH]3)cc3ccccc23)C1]

Step A: (R)-tert-butyl 3-((3-cyanoisoquinolin-1-yl)oxy)pyrrolidine-1-carboxylate A mixture of (R)-tert-butyl 3-hydroxypyrrolidine-1-carboxylate (496 mg, 2.65 mmol) in NMP (4 mL) at 0° C. was treated with NaH (106 mg, 2.65 mmol) and stirred for 1 hour. Next, 1-chloroisoquinoline-3-carbonitrile (500 mg, 2.65 mmol) was added and the reaction mixture was stirred at RT for 15 minutes and then heated at 140° C. for 15 minutes in a microwave reactor. The crude reaction mixture, which contained the title compound, was used directly in the next step.

Step B: (R)-tert-butyl 3-((3-(5-oxo-4,5-dihydro-1H-1,2,4-triazol-3-yl)isoquinolin-1-yl)oxy)pyrrolidine-1-carboxylate

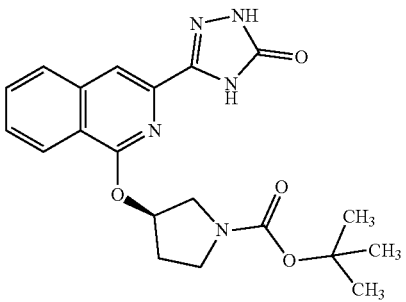 [SMILES: CC(C)(C)OC(=O)N1CC[C@@H](Oc2nc(-c3n[nH]c(=O)[nH]3)cc3ccccc23)C1]

To crude (R)-tert-butyl 3-((3-cyanoisoquinolin-1-yl)oxy)pyrrolidine-1-carboxylate was added ethyl hydrazinecarboxylate (1.104 g, 10.60 mmol). The reaction mixture was heated at 175° C. overnight and was subsequently cooled and diluted with EtOAc. The organic phase was washed with brine, dried over $Na_2SO_4$, and concentrated to give the title compound, which was used directly in the next step.

Step C: (R)-3-(1-(pyrrolidin-3-yloxy)isoquinolin-3-yl)-1H-1,2,4-triazol-5(4H)-one

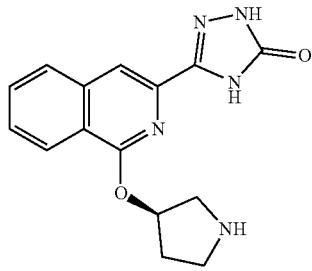 [SMILES: O=c1[nH]nc(-c2cc3ccccc3c(O[C@@H]3CCNC3)n2)[nH]1]

To crude (R)-tert-butyl 3-((3-(5-oxo-4,5-dihydro-1H-1,2,4-triazol-3-yl)isoquinolin-1-yl)oxy)pyrrolidine-1-carboxylate was added a minimal amount of NMP and TFA (2 mL). The solution was stirred at RT for 10 minutes and concentrated. The crude product was purified by preparative HPLC eluting with a gradient of 15-22% ACN in water (acid mode) to give the title compound (229 mg, 29% over 3 steps).

Step D: (R)-3-(1-((1-acryloylpyrrolidin-3-yl)oxy)isoquinolin-3-yl)-1H-1,2,4-triazol-5(4H)-one To a solution of (R)-3-(1-(pyrrolidin-3-yloxy)isoquinolin-3-yl)-1H-1,2,4-triazol-5(4H)-one (11 mg, 0.037 mmol) in DCM (3 mL) was added 2,6-dimethylpyridine (5.80 μL, 0.050 mmol) at 0° C. followed by acryloyl chloride (8.08 μL, 0.100 mmol). The reaction mixture was stirred at RT overnight, forming a white solid. The solids were filtered and dried to give the title compound (4 mg, 23%). H NMR (400 MHz, $CD_3CN$) δ ppm 2.22-2.51 (m, 2H), 3.09-3.17 (m, 1H), 3.68-3.91 (m, 2H), 3.94 (br s, 1H), 4.06 (d, J=12.13 Hz, 1H), 5.60-5.76 (m, 1H), 5.98 (br s, 1H), 6.06 (br s, 1H), 7.47-7.62 (m, 1H), 7.62-7.74 (m, 1H), 7.79 (d, J=7.58 Hz, 1H), 7.92 (d, J=3.79 Hz, 1H), 8.15 (d, J=8.08 Hz, 1H); ESI-MS m/z $[M+H]^+$ 352.0.

TABLE 2, below, lists BTK inhibition data for many of the compounds described in the examples, where larger $pIC_{50}$ values represent higher potency. The compounds were tested in accordance with the assay described in the specification.

TABLE 2

BTK Inhibition ($pIC_{50}$) for Example Compounds

| Example No. | $pIC_{50}$ |
|---|---|
| 1 | >8.7 |
| 2 | 7.1 |

Example 3: Pharmacokinetics Study in Dogs

A pharmacokinetic analysis was conducted in male beagles following oral administration of the compound of Example 1 complexed with CAPTISOL® (Formulations A and E) or formulated in various solid dosage forms (Formulations B, C, and F). Formulation D is a capsule containing a co-crystal of the compound of Example 1. In the formulations, below, the amounts of the compound of Example 1 listed in Tables 3-7 correspond to the desired amount of the compound in the respective formulation (i.e., without impurities).

A. Formulation A (Aqueous CAPTISOL® Solution)

Table 3 lists the components of Formulation A. After dissolving the compound of Example 1 in 0.25M aqueous NaOH solution, a 40% w/v aqueous CAPTISOL® solution was added to obtain a 1:25 (w/w) active compound:CAPTISOL® ratio. The pH was adjusted to 7 using 10% phosphoric acid, resulting in an aqueous solution having an active compound concentration of approximately 7.5 mg/mL. The dosage was set at 100 mg and approximately 13.3 mL was administered orally to each test subject.

TABLE 3

Composition of Formulation A

| Component | Amount |
|---|---|
| Compound of Example 1 | 2.25[1] g |
| 0.25M NaOH (aq) | 36 mL |
| 40% (w/v) CAPTISOL ® | 150 mL |
| 10% (w/w) phosphoric acid (aq) | 4.92 mL |
| Water | q.s. |
| Total | 300 mL |

[1]Amount of Example 1 compound without impurities

Formulation B (Immediate Release Tablet)

Table 4 lists the components of Formulation B. Water was added to a dry mixture of the compound of Example 1, binders and disintegrants. The wet mixture was granulated using a mortar and pestle and then dried to obtain a granulated powder. A lubricant was admixed with the granulated powder and a tabletop tablet molding machine (HANDTAB-200, Ichihashi Seiki Co.) was used to prepare tablets from the resulting powder mixture. Each tablet contained 300 mg of the compound of Example 1 and was formed under a tableting force of 10 kN (total weight ~400 mg, 12 mm long diameter×7 mm short diameter). The dosage was set at 300 mg and one tablet was administered orally to each test subject.

TABLE 4

Composition of Formulation B

| Component | Amount/Tablet |
|---|---|
| Compound[1] of Example 1 | 300 mg |
| Binder[2] | 43 mg |
| Binder/Disintegrant | 30 mg |
| Binder/Disintegrant | 9 mg |
| Binder/Disintegrant | 15 mg |
| Lubricant | 3 mg |
| Water[3] | q.s. |
| Total | 400 mL |

[1]Amount of Example 1 compound without impurities
[2]Nominal amount of binder; actual amount accounts for impurities in the API
[3]Water was removed during processing Formulation C (Physical Mixture of Example 1 Compound and CAPTISOL®):

Table 5 lists the components of Formula C. A 1:25 (w/w) ratio of the compound of Example 1 and CAPTISOL®, microcrystalline cellulose, sodium carboxymethyl starch, and magnesium stearate were mixed using a mortar and pestle. A tabletop tablet molding machine (HANDTAB-200, Ichihashi Seiki Co.) was used to prepare tablets from the resulting powder mixture. Each tablet contained 25 mg of the compound of Example 1 and was formed under a tableting force of 12 kN (total weight ~700 mg, 18.5 mm long diameter×9 mm short diameter). The dosage was set at 100 mg and four tablets were administered orally to each test subject.

TABLE 5

Composition of Formulation C

| Component | Amount/Tablet |
|---|---|
| Compound[1] of Example 1 | 25 mg |
| CAPTISOL ® | 625 mg |
| Microcrystalline cellulose[2] | 15 mg |
| Sodium carboxymethyl starch | 30 mg |
| Magnesium stearate | 5 mg |
| Total | 700 mL |

[1]Amount of Example 1 compound without impurities
[2]Nominal amount; actual amount accounts for impurities in the API Formulation D (Co-Crystal Capsule)

A gelatin capsule containing a co-crystal of the compound of Example 1 was prepared. Each capsule contained 100 mg of the compound of Example 1 (144 mg of co-crystal). One capsule was administered orally to each test subject.

Formulation E (CAPTISOL® Spray-Dried Dispersion Tablet)

Table 6 lists the components of Formula E. Aqueous Formulation A, above, was spray dried using a PSD-1 spray drier (GEA Niro) to obtain a solid complex of the compound of Example 1 and CAPTISOL®. The complex was admixed with light anhydrous silicic acid and magnesium stearate using a mortar and pestle. A tabletop tablet molding machine (HANDTAB-200, Ichihashi Seiki Co.) was used to prepare tablets from the resulting powder mixture. Each tablet contained 25 mg of the compound of Example 1 and was formed under a tableting force of 12 kN (total weight ~711 mg, 18.5 mm long diameter×9 mm short diameter). The dosage was set at 100 mg and four tablets were administered orally to each test subject.

TABLE 6

Composition of Formulation E

| | Component | Amount/Tablet |
|---|---|---|
| Spray dried powder | Compound[1] of Example 1 | 25 mg |
| | CAPTISOL ® | 667 mg |
| | NaOH | 4 mg |
| | phosphoric acid | 5.47 mg |
| Excipients | Light anhydrous silicic acid | 5 mg |
| | Magnesium stearate | 5 mg |
| | Total | 711.47 mg |

[1]Amount of Example 1 compound without impurities in spray dried powder

Formulation F (Solid Dispersion Tablet)

Table 7 lists the components of Formula F. The compound of Example 1 and hypromellose phthalate were dissolved at a ratio of 1:40 (w/w) in dimethyl sulfoxide. The resulting solution was lyophilized using a freeze dryer (FDU-2100, EYELA) to obtain a solid dispersion powder, which was granulated using a mortar and pestle. The granulated powder was admixed with D-mannitol, microcrystalline cellulose, croscarmellose sodium, light anhydrous silicic acid, and magnesium stearate. A tabletop tablet molding machine (HANDTAB-200, Ichihashi Seiki Co.) was used to prepare tablets from the resulting powder mixture. Each tablet contained 25 mg of the compound of Example 1 and was formed under a tableting force of 15 kN (tablet total weight ~600 mg, 16 mm long diameter×9 mm short diameter). The dosage was set at 100 mg and four tablets were administered orally to each test subject.

TABLE 7

Composition of Formulation F

| Component | Amount/Tablet |
|---|---|
| Compound[1] of Example 1 | 25 mg |
| Hypromellose phthalate | 100 mg |
| D-mannitol | 360 mg |
| Microcrystalline cellulose | 60 mg |
| Croscarmellose sodium | 40 mg |
| Light anhydrous silicic acid | 9 mg |
| Magnesium stearate | 6 mg |
| Total | 600 mL |

[1]Amount of Example 1 compound without impurities

Each formulation described above was administered orally to a fasting beagle (one-year old male, five test subjects per formulation). A pentagastrin solution was administered to each test subject 15 minutes prior to the administration of drug. Blood samples were taken at 15 and 30 minutes, and at 1, 2, 4, 6, 8, 12, and 24 hours after administration of drug. Plasma was obtained using centrifugation. The concentration of Example 1 compound in plasma was measured using LC and MS/MS under the conditions listed in Tables 8 and 9, respectively.

TABLE 8

| LC conditions | |
|---|---|
| Analytical column | Kinetex C18, 50 mm × 2.0 mm I.D., 2.6 μm (Phenomenex) |
| Column oven temperature | 40° C. |
| Mobile phase | Purified water/acetonitrile/formic acid (600:200:0.1, v/v/v) |
| Flow rate | 0.2 mL/minute |
| Injection volume | 20 μL |
| Auto sampler temperature | 10° C. |
| Rinsing solution | Acetonitrile/purified water/formic acid (600:400:0.1, v/v/v) |
| Run time | 5.0 minutes |

The Effluent from 2.0 to 5.0 minutes was transferred to the MS/MS by valve operation.

TABLE 9

| MS/MS conditions | |
|---|---|
| Ionization mode | Turbo ion spray |
| Polarity | Positive |
| Scan type | Selected reaction monitoring (SRM) |

TABLE 9-continued

| MS/MS conditions | |
|---|---|
| Ion spray voltage (IS) | 5500 V |
| Turbo probe temp. (TEM) | 600° C. |
| Interface heater (ihe) | ON |
| Curtain gas pressure (CUR) | 0.28 MPa (40 psi, $N_2$) |
| Ion source gas 1 pressure (GS1) | 0.28 MPa (40 psi, Air) |
| Ion source gas 2 pressure (GS2) | 0.28 MPa (40 psi, Air) |
| Collision gas pressure (CAD) | 8 Bit ($N_2$) |
| Dwell time | 0.8 seconds (for compound of Example 1) |
| | 0.2 seconds (for internal standard) |
| Duration time | 5.0 minutes |

| Monitor ion and parameters | Precursor ion (m/z) | → | Product ion (m/z) | DP[1] (V) | EP[2] (V) | CE[3] (V) | CXP[4] (V) |
|---|---|---|---|---|---|---|---|
| Compound of Example 1 | 352.3 | → | 124.1 | 131 | 10 | 23 | 20 |
| Internal Standard | 355.0 | → | 127.2 | 106 | 10 | 23 | 18 |

[1]Declustering Potential,
[2]Entrance Potential,
[3]Collision Energy,
[4]Collision Cell Exit Potential FIG. 1 shows the mean concentration of the compound of Example 1 in blood plasma as a function of time following oral dosing of dogs with Formulations A, B, C, D, E, and F. The maximum concentration of the active compound in blood ($C_{max}$) and the time to reach the maximum concentration of the drug in blood ($t_{max}$) were measured using the concentration vs. time curves. The concentration of the drug in blood from 0 to 24 hours and the area under the concentration-versus-time curve ($AUC_{0-24\,h}$) were calculated using a linear trapezoidal method. Table 10 lists pharmacokinetic data (average values (S.D.)).

TABLE 10

| | Dog Pharmacokinetics | | | |
|---|---|---|---|---|
| Formulation | Dose (mg/subject) | $t_{max}$ (h) | $C_{max}$ (ng/mL) | $AUC_{0-24\,h}$ (ng · h/mL) |
| A | 100 | 0.8 (0.3) | 1251.4 (717.2) | 2353.0 (864.9) |
| B | 300 | 1.6 (0.5) | 4.7 (1.0) | 30.2 (14.5) |
| C | 100 | 0.6 (0.2) | 9.3 (1.3) | 36.9 (1.7) |
| D | 100 | 1.3 (0.7) | 229.0 (106.5) | 585.5 (231.6) |
| E | 100 | 0.9 (0.3) | 1133.3 (679.5) | 1994.6 (798.7) |
| F | 100 | 0.4 (0.1) | 51.5 (29.8) | 130.2 (88.3) |

Example 4: Dissolution Test

Figure 2:
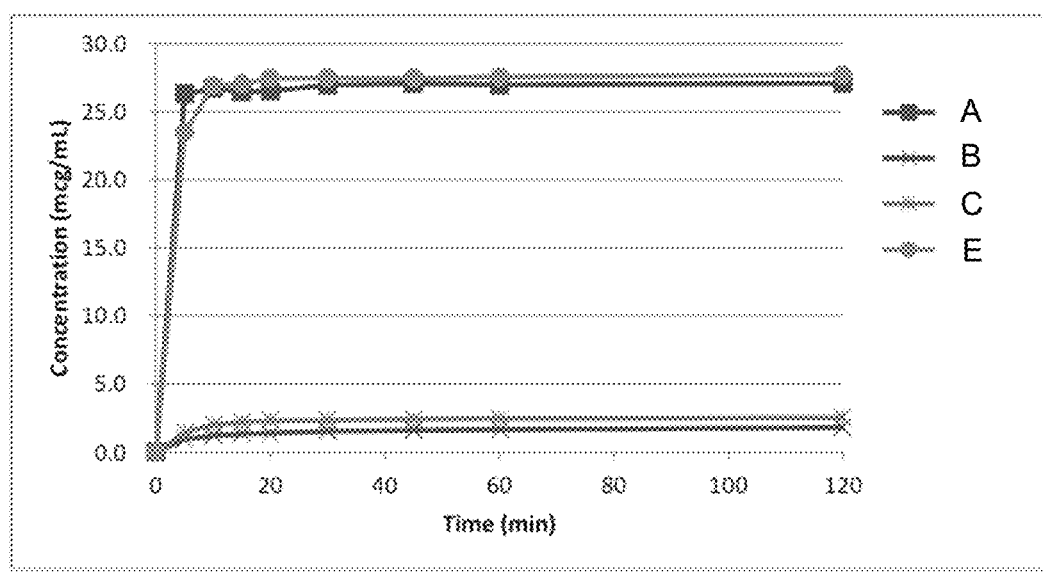
FIG. 2 shows the mean eluent concentration of the compound of Example 1 as a function of time for Formulations A, B, C, and E, which were evaluated in the Japanese Pharmacopoeia Dissolution Test.

FIG. 2 shows the mean eluent concentration of the compound of Example 1 as a function of time for Formulations A, B, C, and E, which were evaluated in the Japanese Pharmacopoeia Dissolution Test using the paddle method. The test was performed in 900 mL of the Japanese Pharmacopoeia Test Fluid No. 2 for the dissolution test (pH=6.8) using an NTR 6200AT dissolution testing apparatus (Toyama Co., Ltd.) with a paddle rotation speed of 100 rpm. For each formulation, test samples were collected at prescribed time points, filtered through a 0.45 μm polypropylene membrane filter (GHP Acrodisc Glass Fiber Pre-filter, PALL), and diluted in dimethyl sulfoxide. The eluent concentration of the compound of Example 1 was measured using UPLC under conditions described in Table 11.

TABLE 11

| UPLC conditions | |
|---|---|
| Analytical column | Waters Acquity BEH C18, 100 mm × 2.1 mm, 1.7 μm |
| Column temperature | 50° C. |
| Detection | UV @ 250 nm |
| Mobile phase | 0.025% TFA in Water/0.02% TFA in acetonitrile (7/3, v/v) |
| Flow rate | 0.3 mL/minute |
| Injection volume | 1 μL |
| Auto sampler temperature | 25° C. |
| Rinsing solution | Acetonitrile/purified water (1/1, v/v) |
| Run time | 4.0 minutes |

As used in this specification and the appended claims, singular articles such as "a," "an," and "the," may refer to a single object or to a plurality of objects unless the context clearly indicates otherwise. Thus, for example, reference to a composition containing "a compound" may include a single compound or two or more compounds. It is to be understood that the above description is intended to be illustrative and not restrictive. Many embodiments will be apparent to those of skill in the art upon reading the above description. Therefore, the scope of the invention should be determined with reference to the appended claims and includes the full scope of equivalents to which such claims are entitled. The disclosures of all articles and references, including patents, patent applications and publications, are herein incorporated by reference in their entirety and for all purposes.

What is claimed is:

1. A complex comprising a compound of Formula 1,

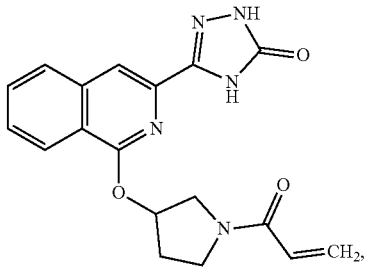

a stereoisomer thereof or a tautomer of the compound of Formula 1, and
a sulfobutylether β-cyclodextrin, wherein the complex is an amorphous solid.

2. The complex according to claim 1, wherein the compound is (S)-3-(1-((1-acryloylpyrrolidin-3-yl)oxy)isoquinolin-3-yl)-1H-1,2,4-triazol-5(4H)-one or a tautomer thereof.

3. The complex according to claim 1, wherein the compound is (R)-3-(1-((1-acryloylpyrrolidin-3-yl)oxy)isoquinolin-3-yl)-1H-1,2,4-triazol-5(4H)-one or a tautomer thereof.

4. The complex according to claim 1, wherein the sulfobutylether β-cyclodextrin and the compound of Formula 1, stereoisomer or tautomer thereof are present in a molar ratio of about 1:1 to about 10:1.

5. The complex according to claim 1, wherein the sulfobutylether β-cyclodextrin and the compound of Formula 1, stereoisomer or tautomer thereof are present in a molar ratio of about 1:1 to about 5:1.

6. The complex according to claim 1, wherein the sulfobutylether β-cyclodextrin and the compound of Formula 1, stereoisomer or tautomer thereof are present in a molar ratio of about 1:1.

7. A pharmaceutical composition comprising a complex as defined in claim 1, and a pharmaceutically acceptable excipient.

8. A method of making the complex of claim 1 comprising the compound of Formula 1,

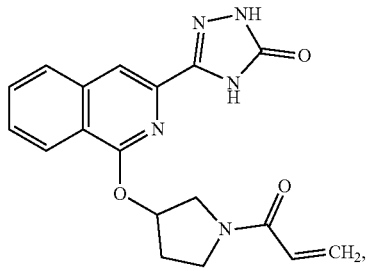

a stereoisomer thereof or a tautomer of the compound of Formula 1, and a sulfobutylether β-cyclodextrin, wherein the complex is an amorphous solid, the method comprising:
atomizing a liquid solution into droplets, the liquid solution comprising the compound, stereoisomer, or tautomer of Formula 1, the sulfobutylether β-cyclodextrin, and water; and
removing at least a portion of the water from the droplets to form the complex.

9. The method according to claim 8, wherein the liquid solution was obtained by dissolving the compound of Formula 1, stereoisomer or tautomer thereof in water having a pH of about 12 or greater.

10. The method according to claim 9, wherein the liquid solution was obtained by dissolving the compound of Formula 1, stereoisomer or tautomer thereof in water having a pH of about 13 or greater.

11. The method according to claim 8, wherein the pH of the liquid solution was adjusted to a pH of about 7 before atomizing the liquid solution into droplets.

* * * * *